United States Patent [19]

Wallace

[11] Patent Number: 5,185,244
[45] Date of Patent: Feb. 9, 1993

[54] GENETIC TEST FOR HEREDITARY NEUROMUSCULAR DISEASE

[75] Inventor: Douglas C. Wallace, Atlanta, Ga.

[73] Assignee: Emory University, Atlanta, Ga.

[21] Appl. No.: 447,679

[22] Filed: Dec. 8, 1989

[51] Int. Cl.$^5$ .................. C12Q 1/68; C12P 19/34; G01N 33/48; C07H 15/12
[52] U.S. Cl. .......................... 435/6; 435/91; 436/63; 436/94; 436/501; 536/23.1; 536/24.31
[58] Field of Search ............ 435/6, 91, 194; 436/501, 94, 63; 536/26, 27, 28, 29; 935/77, 78

[56] References Cited

PUBLICATIONS

Singh et al., The New England Journal of Medicine 320 (20):1300–1305 (may 18, 1989).
Wallace et al., Science 242:1427–1430 (Dec. 9, 1988).
Wallace et al., Am. J. Hum. Genet. 38:461–481, 1986.
Wallace, Somatic Cell & Mol. Genet. 12:41–49, 1986.
Wallace et al., Achievements and Perspectives of Mitochondrial Research, vol. 2:427–435, 1985.
Johnson et al., J. Mol. Evol. 19:255–271, 1983.
Blanc et al., Am. J. Hum. Genet. 35:167–176, 1983.
Wallace et al., Hum. Genet. 1681:145–147, 1982.
Denaro et al., Proc. Natl. Acad. Sci. 78:5768–5772, 1981.

Primary Examiner—Margaret Moskowitz
Assistant Examiner—Stephanie W. Zitomer
Attorney, Agent, or Firm—Needle & Rosenberg

[57] ABSTRACT

The present invention relates a method and manufacture for detecting neuromuscular disease, particularly Leber's hereditary optic neuropathy, by ascertaining whether a point mutation has occurred at the 11778 nucleotide position in the mitochondrial DNA of a patient. The invention provides methods to detect this mutation including digestion of the patient's mtDNA with restriction endonucleases followed by analysis of the resulting fragments, differential hybridization of oligonucleotides procedures, and differential PCR techniques.

36 Claims, No Drawings

GENETIC TEST FOR HEREDITARY NEUROMUSCULAR DISEASE

ACKNOWLEDGEMENT

The invention described herein was made with Government support under grant no. NS21328 awarded by the National Institutes of Health. The Government has certain rights in this invention.

BACKGROUND OF THE INVENTION

The present invention relates to a method of detecting neuromuscular disease in a patient, particularly Leber's hereditary optic neuropathy. More particularly, the invention relates to the detection of a point mutation at the mitochondrial DNA nucleotide position 11778 in the patient's DNA.

Leber's hereditary optic neuropathy (LHON) is associated with a rapid bilateral loss of central vision caused by neuroretinal degeneration. The median age at the onset of vision loss is 20 to 24 years, but ranges from adolescence to late adulthood. Cardiac dysrhythmias are also a frequent manifestation. In numerous large pedigrees, LHON patients have been found to be related exclusively through the maternal lineage. However, in most pedigrees, expression is variable and there is a bias toward males exhibiting ophthalmological problems.

Human mitochondrial DNA (mtDNA) is also maternally inherited. Each cell contains thousands of copies of mtDNA in the matrixes of the mitochondria. Each mtDNA codes for a large and a small ribosomal RNA, 22 transfer RNA's, and 13 polypeptides that function in the enzyme complexes of oxidative phosphorylation, including subunit 4 of NADH dehydrogenase.

A broad spectrum of neuromuscular diseases has recently been associated with alterations in mitochondrial structure and in the capacity to generate ATP. Some of these "mitochondrial encephalomyopathies," such as LHON, primarily affect the central nervous system, but others, such as myoclonus epilepsy and ragged red fiber disease (MERRF) or mitochondrial encephalomyopathy lacticacidoses and stroke-like symptoms (MELAS), affect the skeletal muscle, heart, kidney, and liver as well. Diagnoses of multiple sclerosis and LHON may be sometimes confused.

Prior to this invention, no method was known for the molecular diagnosis of LHON or associated diseases. Therefore, there exists a need to establish the molecular cause of such disease and to provide a specific molecular test to accurately diagnose the presence of or susceptibility to the disease in a patient.

SUMMARY OF THE INVENTION

The present invention relates to the discovery of a specific nucleotide substitution in mtDNA at nucleotide position 11778 (nt11778) which changes the highly conserved 340th amino acid of the NADH dehydrogenase subunit number 4 from an arginine to a histidine. This mutation also eliminates an SfaN1 restriction site, thus providing a simple diagnostic test for the presence of the mutation. Also, a Mae 3 restriction site is created by the mutation, providing an alternative restriction enzyme test.

A survey of restriction-fragment-length polymorphisms in the mtDNA of families that are afflicted with LHON and of controls confirm that this mutation is associated with LHON but has never been found in persons outside LHON pedigrees. Furthermore, a genetic analysis of a phylogenetic tree for mitochondrial DNA polymorphism and sequence variants from three probands with LHON and four controls reveals that this mutation must have arisen twice independently, once in an American black individual and once in a European white individual. Because the mutation correlates with LHON symptoms in both populations, these findings indicate that the mutation is a cause of the disease.

Thus, the present invention provides a method for detecting LHON and associated neuromuscular diseases in a patient by testing the mtDNA in any cell from the patient for the presence of a point mutation at the mtDNA nt11778. That mutation is detected by digesting the patient's mtDNA with a restriction endonuclease followed by analysis of the resulting fragments. Alternatively, the presence of the point mutation is detected by either differential hybridization of oligonucleotides or differential polymerase chain reaction (PCR) procedures.

More particularly, all or part of the patient's mtDNA can be digested with SfaN1 followed by analysis of the resulting fragments to determine whether the mtDNA is cut at nt11778. If the mtDNA is cut at this site, the mtDNA is normal; if not, the mtDNA has the disease causing mutation. The cutting of the DNA at this site can be assessed by appropriate procedures such as separating the DNA fragments by agarose electrophoresis followed by Southern blotting, end-labeling the fragments followed by polyacrylamide gel electrophoresis, or amplification of purified, crude, or enriched mtDNA samples preceeding the digestion by the endonuclease and separation of the digested products on agarose gels.

The presence of a point mutation at nt11778 can also be detected by the differential hybridization of oligonucleotides. An oligonucleotide probe is constructed that is complementary to the nucleotide sequence on one strand surrounding nt11778 for either normal mtDNA or mutant mtDNA. A probe that is complementary to the mutant strand hybridizes with a patient's mtDNA only if the patient possesses the nt11778 mutation. Conversely, a probe that is complementary to the normal strand hybridizes with a patient's mtDNA only if the patient does not possess the disease causing mutation. Thus, the extent of hybridization of either probe defines whether the patient possesses the disease causing mutation.

Furthermore, differential PCR can be used to detect the presence of the point mutation. For both normal mtDNA or mutant mtDNA, an oligonucleotide PCR primer is constructed such that the 3' end of the primer is located at nt11778. Two other primers are constructed such that they flank the nt11778 position. All four primers and a mtDNA sample from a patient are allowed to react in a PCR. The primers that are complementary to normal mtDNA allow amplification of a patient's mtDNA only if that mtDNA does not possess the nt11778 mutation. Conversely, primers that are complementary to mutant mtDNA allow amplification only if the patient's mtDNA possesses the point mutation. Thus, analysis of the end products of a PCR using these primers determines whether the point mutation is present in the patient's mtDNA.

Accordingly, one of the objectives of this invention is to provide a method of detecting neuromuscular disease, particularly LHON, in a patient. A further object of this invention is to provide a method to test any cell of a patient for the presence of a point mutation at nt11778 in the patient's mtDNA.

Furthermore, this invention provides a method to assay whether a point mutation exists at nt11778 of a patient's mtDNA by digesting a sample of the patient's mtDNA with a restriction endonuclease followed by determining the length of the resulting mtDNA fragments. The patient's mtDNA sample can contain either complete or partial mtDNA and may be either crude, purified, or amplified mtDNA.

Still further, this invention provides a differential oligonucleotide hybridization method for assaying whether a point mutation exists at nt11778 of a patient's mtDNA. This method involves hybridizing a sample of the patient's mtDNA with either an oligonucleotide probe that is complementary to normal mtDNA or one that is complementary to mutant mtDNA in the region surrounding nt11778. The patient's mtDNA sample can contain either complete or partial mtDNA and may be either crude, purified, or amplified mtDNA.

A still further object of this invention is to provide a differential PCR method for assaying whether a point mutation exists at nt11778 of a patient's mtDNA. This method involves analysis of the end products of a PCR that employs a sample of the patient's mtDNA and four oligonucleotide primers. One primer is specific to normal mtDNA and one is specific to mutant mtDNA; both of these primers are constructed such that the 3' end of the primer is located at nt11778. The patient's mtDNA sample can contain either complete or partial mtDNA and may be either crude, purified, or amplified mtDNA.

These and other objects and advantages of the present invention are apparent to person skilled in the art from the following detailed description.

DETAILED DESCRIPTION OF THE INVENTION

1. Identification of the nt11778 Mutation as a Cause of LHON

As used herein, amplified DNA refers to DNA that has been reproduced using a PCR technique; enriched DNA refers to a DNA sample that has been concentrated.

As described in *Science* 242:1427 (1988), incorporated herein by reference, candidate mutations for LHON were sought by cloning and sequencing the mtDNA from the blind proband of a large, black LHON pedigree from Georgia. Because most reported LHON pedigrees are Caucasoid, analysis of a black LHON mtDNA minimized the chances of associating the disease with a rare ethnic-specific sequence polymorphism. Eighty-five percent of the LHON mtDNA coding region was sequenced. Comparison with the "normal" Cambridge mtDNA sequence, *Nature* 290:457 (1981), revealed 25 base substitutions, 8 of which altered amino acids.

A replacement mutation in the LHON mtDNA sequence is implicated in the disease if it (i) changes a highly evolutionarily conserved amino acid, (ii) is frequently found in LHON patients, and (iii) is not found in normal individuals from the general population. Seven of the mutations, nt8701, nt9163, nt9559, nt10398, nt13702, nt14199, and nt12385, did not fulfill these criteria and thus are unlikely to be causally related to LHON.

The mutation at nt11778 in NADH dehydrogenase subunit 4 converts a guanidine in the Cambridge sequence to an adenine in the LHON mtDNA. This changes the 340th amino acid from an arginine to a histidine. This arginine is highly conserved between species. The mutation also removes an SfaN1 site and thus can be readily identified by SfaN1 digestion of a 212-bp PCR fragment encompassing the mutation. The PCR fragments of the Georgia LHON maternal lineage were not cut with SfaN1, a result consistent with the sequence data. However, the amplified mtDNAs from the spouses were cut into the expected 117- and 95-bp fragments. The origin of the 212- and 117-bp fragments was verified by hybridization with an oligonucleotide probe homologous to an internal sequence. Amplified mtDNAs from ten controls and six LHON patients revealed that all controls retained the SfaN1 site, whereas all LHON patients lacked the site. Hence, the nt11778 mutation correlates with LHON.

To determine the generality of this relation, a total of 45 independent controls (10 blacks, 10 Asians, 14 Caucasians, and 11 Finns) were tested. Every control sample retained the SfaN1 site.

These control results were compared to those of 11 independent LHON lineages. The LHON pedigrees were collected from diverse geographic and ethnic backgrounds so that it would be unlikely that they would all by chance harbor the same rare ethnic mtDNA restriction fragment length polymorphism. Nine of the 11 LHON pedigrees lacked the SfaN1 site. Four of these were from different regions of North America. From the Georgia pedigree, 13 maternal relatives were tested, 7 of whom were blind. All lacked the SfaN1 site. From a Michigan pedigree, five maternal relatives were tested; two were blind and all lacked the SfaN1 site. From a Maryland pedigree, the blind proband was examined and he lacked the site. Finally, from a Canadian pedigree, a blind brother and sister were tested, and both lacked the site. The five remaining LHON pedigrees that lacked the site were from Finland. One blind member from each of four Finnish pedigrees were tested and all four lacked the site. Eight maternal relatives, seven blind and one with microangiopathy, in an additional Finnish pedigree were examined. All of these individuals lacked the site.

Two of the 11 LHON pedigrees were discordant, however. The first of these was from the Human Genetic Mutant Cell Repository (Camden, New Jersey). Cell line GM3857, derived from one of two blind brothers, was tested and it retained the SfaN1 site. The second was a large pedigree from Finland with multiple affected individuals. Two blind cousins were tested and both retained the site. Even with these discordant cases, however, the association between LHON and the nt11778 mutation was highly significant ($P \leq 0.001$ by $X^2$ test). Five points support the hypothesis that the mtDNA mutation at nt11778 is the cause of LHON. First, both LHON and the mtDNA are exclusively maternally inherited. Second, the nt11778 mutation is found in multiple independent LHON lineages, but not in numerous unaffected control lineages. Third, the nt11778 mutation changes a highly conserved amino acid in a region of the genome where there is a greater that 85% amino acid homology between mouse, cow, and human. Fourth, all other observed LHON mtDNA substitutions were ruled out. Fifth, the mutation would alter, but probably not eliminate, the respiratory function of NADH dehydrogenase subunit 4. This dysfunction could mimic the effects of chronic respiratory inhibitor treatment.

Although the nt11778 mutation does result in LHON, the existence of two discordant pedigrees implies that it may not be the only cause. This implication was confirmed by analyzing four individuals from a LHON plus infantile bilateral striatal necrosis (IBSN) pedigree in which optic neuropathy without presymptomatic microangiopathy is associated with dystonic rigidity and basal ganglial lesions. All four LHON plus IBSN individuals retained the SfaN1 site, confirming that this disease is different from LHON. The two discordant "LHON" pedigrees might then be LHON plus IBSN pedigrees that have not yet expressed the IBSN phenotype, or they may be the product of an alternative mutation that can result in LHON.

Although there is an excellent correlation between LHON and the loss of the SfaN1 site between maternal lineages, there is a much less clear association between the loss of the SfaN1 site and the optic atrophy and cardiac dysrhythmia observed within pedigrees. Because the nt11778 mutation was found to be homoplasmic in all LHON pedigrees examined, the variable symptoms cannot be the result of replicative segregation of a mixed mutant and wild-type mtDNA population. Therefore, the nt11778 mutation appears to be necessary but not sufficient for overt symptoms.

This conclusion implies that additional factors are involved in the expression of the mutant phenotype. The sex bias in symptoms could result from a sex-related physiological difference, an X-chromosome dosage effect, or a recessive X-linked modulating gene. Furthermore, environmental stresses that reduce respiratory capacity, for example, smoking, might augment the expression of the mutation. If this is the case, then it is possible that metabolic therapies that increase cellular respiratory metabolism might reduce the risk of deleterious symptoms in as yet unaffected family members.

To confirm that the mutation at nt11778 causes LHON rather than being merely a linked polymorphism, a detailed analysis of the mitochondrial DNA character states of the probands from three affected families, their unaffected familial controls, and HeLa cells was performed as discussed in *New Eng. J. Med.* 320:1300 (1989), incorporated herein by reference. If the mutation was simply a rare linked polymorphism, then all affected mitochondrial DNAs that had that mutation must have been related through one female founder whose mitochondrial DNA carried the nt11778 polymorphism. This would mean that all affected mitochondrial DNAs should have a common haplotype, sharing multiple character states. Alternatively, if the SfaN1 mutation was the one causing LHON, then it could be associated with as many different mitochondrial DNA haplotypes as there have been independent mutations.

The mitochondrial DNAs from the patient cell line and their respective controls were digested with 11 restriction endonucleases. Individual nucleotide changes (character states), identified by restriction-fragment-length polymorphisms (RFLPs) or oligonucleotide hybridization, were assumed to be independent and to accumulate randomly in the mitochondrial DNA over time. The sum of all the character states for a particular mitochondrial DNA is called its haplotype. Because all human mitochondrial DNAs are known to be derived from a common ancestor, the historical relation between extant mitochondrial DNAs can be reconstructed on the basis of the proportion of character states they share. The greater the number of differences, the longer the time since two mitochondrial DNAs had a common ancestor.

These relations were diagramed within a phylogenetic tree using the parsimony computer program PAUP to generate unbiased minimal-distance trees. Two evolutionary trees of equal probability (0.933) were generated. The primary differences between the two trees are the relative positions of mutations at nt8701 and nt11778. In the first tree, the mutation at nt8701 differentiates the mtDNAs from the white and the black subjects. This arrangement is strongly supported by an extensive analysis of the racial distribution of this ATPase 6 mutation. A survey of 15 subjects (two Africans, three black Americans, two Chinese, and eight white Europeans and Americans) revealed that the polymorphism at nt8701 precisely distinguishes the white Europeans and Americans from the Africans, the black Americans, and the Asians. If the mutation at nucleotide 8701 is positioned between the white and black subjects, then the nt11778 mutation must have occurred twice, thus linking the unaffected European and black American controls with their respective family members who have LHON.

In the alternative tree, the mtDNAs of the affected patients and the unaffected controls are separated into two independent lineages, one of which has the nt11778 mutation and one of which does not. This arrangement is untenable for two reasons. First, it means that the mutation at nt8701 arose twice—once in a lineage of normal mtDNA's and once in a lineage of mtDNAs associated with LHON. This is extremely improbable because the mutation at nt8701 correlates highly with human racial groups, suggesting that is occurred once when the European mtDNAs separated from the African and Asian mtDNAs. Furthermore, this mutation changes an amino acid in the highly conserved ATPase 6 gene, which would be a very rare event.

Second, the tree suggests that the nt11778 mutation is quite old, encompassing both blacks and whites and having almost as many mutation steps as those that separate the mtDNAs from the European subjects from those of the two black Americans. By comparing a 10,127 base pairs of mtDNA from one of the affected black American patients with the published European sequence of the same regions, the overall range for the age of the nt11778 mutation in this second tree is 39,000 to 109,000 years. If the mutation had existed in the human population this long, then it should be widely dispersed throughout the world. However, a random survey of 52 subjects from all three major racial groups revealed that not one had the nt11778 mutation. Hence, the nt11778 mutation must be recent, thus eliminating tree 2.

Because the validity of tree 1 is shown, the nt11778 mutation must have occurred at least twice. In both instances, the mutation was associated with blindness and, therefore, the mutation at nt11778 must cause LHON.

2. Detection of the nt11778 Point Mutation a. Methods for obtaining mtDNA

Mitochondrial DNA can be derived from any cell from the patient by various methods; thus, mtDNA can be isolated from a variety of biological samples. For instance, a small platelet pellet can be placed in distilled water and heated to boiling to release the mtDNA. Alternatively, blood can be fractionated on Ficoll-Hypaque gradients (Pharmacia, Piscataway, N.J.) followed by transforming the lymphocytes with Epstein-Barr virus as disclosed in *Am. J. Hum. Genet.* 38:461 (1986). Purified mtDNA can be obtained from these cells by enriching whole-cell lysates through precipitation of the chromatin with 1 M NaCl. The mtDNA-rich supernatant can be further purified by proteinase digestion and organic extraction as disclosed in *Somat. Cell Mol. Genet.* 12:41 (1986). Alternatively, mtDNAs can be purified from isolated mitochondria by detergent lysis and separation with the use of two density-gradient centrifugations with a cesium-chloride-ethidium bromide solution.

The following procedure works well for 50μl whole blood (collected in sodium heparin, EDTA, acid citrate dextrose, or lithium heparin), platelets and lymphocytes left over from fractionation of whole blood, dried blood spots, hair roots, fibroblasts, homogenized brain, homogenized muscle, and amniocytes. Dried blood spots on filter paper, such as Guthrie spots, may be used in this procedure by adding 190 μl of doubly-distilled H$_2$O to the paper folded up in a 1.5 mt centrifuge tube. Similarly, 3–4 plucked hairs may be used. With such extremely limited samples, 25–50% of the DNA recovered should be used in a PCR reaction. When starting with as little as 50–190 μl of whole blood, however, 5 μl of the final suspension is adequate for amplification in a Leber's PCR diagnostic test.

Doubly-distilled H$_2$O is added to the sample to bring the volume to 190 μl. 200 μl 50 mMTris, 2mM EDTA, 1% SDS ("TE-SDS") lysis buffer are added. Following the addition of 10 μl of 10 mg/ml Protease K, the sample is incubated at 55° C. overnight (or for at least 2 hours). The sample is incubated at 93°-95°-C. for 10 minutes to inactivate the Protease K. 100 μl of 2 mg/ml RNAse A (can use 120 μg minimum) is added and the sample is incubated for 5 minutes at room temperature. Following the addition of 100 μl 600mM NaOH, the sample is inverted to mix. 300 μl of 2.55 M potassium acetate, pH 4.8, is then added. The mixture is spun for 15 minutes at 4° C. The supernatant can be further purified by either phenol extraction and alcohol precipitation, as described below, or Geneclean (adsorption matrix manufactured by BIO 101, LaJolla, Calif.) or Qiagen tip 20 (DNA anion exchange resin, made by QIAGEN, Inc., Studio City, Calif.).

The phenol extraction consists of adding a volume of phenol/chloroform equal to the supernatant volume and extracting the proteins by vortexing or shaking the tube followed by spinning for 5 minutes. The supernatant is transferred to a Centricon-100 (Amicon, Danvers, Mass.), the volume is brought up to 2 ml with doubly-distilled H$_2$O, and the supernatant is spun at 3000 rpm for 30–40 minutes. After the filtrate is discarded, the Centricon-100 unit is inverted into a retentate cup and spun at 2000 rpm for 10–15 minutes to recover the DNA in about 40 μl. The procedures involving the Centricon-100 are repeated 2 more times.

Alternatively, instead of utilizing the Centricon-100 procedures, the supernatant can be transferred to a new tube and two volumes of 100% ETOH added. Following mixing, the mixture is allowed to precipitate at −20° or −80° C. for 1 hour. The mixture is spun in the cold for 30 minutes and the supernatant is poured off. 70% ETOH is added, the cap is closed, and the tube is inverted several times. Following a 10 minute spin in the cold, the supernatant is poured off and the pellet is dried in a speed vacuum for approximately 10–15 minutes.

b. Restriction Endonuclease Procedures

Blood samples were obtained from a Leber's patient and his spouse. Both blood samples were fractionated on Ficoll-Hypaque gradients and the lymphocytes were transformed with Epstein-Barr virus. Mitochondrial DNAs were obtained as disclosed above and examined the following three ways.

First, the cesium chloride-ethidium bromide purified mtDNAs were digested with SfaN1 and end labeled with P=(endlabeled by the method disclosed in *Proc. Nat'l Acad. Sci. USA* 77:3605 (1980)). Electrophoresis of the resulting fragments on a 3.5% polyacrylamide gel followed by autoradiography revealed a 679-bp and a 915-bp fragment in the sample obtained from the spouse of the Leber's patient; a corresponding 1594-bp (679+915) fusion fragment was found in the Leber's patient's sample. These results confirmed the loss of the SfaN1 site at nt11778 in the Leber's patient.

Second, either purified or enriched mtDNA samples were digested with SfaN1 and run on a 1.4% agarose gel overnight. The DNA was transferred from the gel to a nylon membrane by Southern blotting. A DNA probe was prepared containing the NADH dehydrogenase subunit 4 gene (containing at least the mitochondrial nucleotides 10863-12457). This probe was end-labeled with gamma-P$^{32}$ and used to hybridize with the mtDNA samples. Autoradiography of the filter showed that the Leber's patient had the 1594-bp fusion fragment and the non-affected spouse had the normal 697 and 915-bp fragments.

Third, purified, crude, or enriched mtDNA samples were subjected to PCR with primers encompassing nt11141-12567. A 1435-bp fragment was obtained for both the Leber's patient and his non-affected spouse. These PCR products were digested with SfaN1 and run on a 1.3% ethidium bromide-stained agarose gel to reveal 679, 638, and 119-bp fragments for the spouse and 1317 and 119-bp fragments for the Leber's patient, again showing the presence of a fusion DNA fragment as a marker for the disease.

The same experiment may be repeated using Mae 3 instead of SfaN1 as the restriction endonuclease. The digested mtDNA from the Leber's patient would have 613, 511, 131, 124, and 57-bp fragments; the normal individual would have 613, 511, 255, and 57-bp fragments. These results confirm that a new site is created in the Leber's patient's mtDNA, yielding 131 and 124-bp fragments versus a 255-bp fragment found in normal mtDNA.

c. Differential Hybridization of Oligonucleotides

Enriched or PCR amplified mtDNA samples can be prepared from test individuals as described above. Oligonucleotides can be prepared complementary to both Leber's and normal mtDNA sequences that include the nucleotide 11778. The Leber's oligonucleotide can be TCACAGTCACATCATAATC (nt11770-11788, 19 bases inclusive, nt11778 underlined); the wild-type oligonucleotide can be GATTATGATGCGACTGTGA (nt11778-11770, 19 bases inclusive, nt11778 underlined). The probes are designed on the DNA strand appropriate to eliminate promiscuous G-T hybridization by avoiding the use of G or T at the informative position. Enriched mtDNA samples from Leber's patients and their spouses are spotted onto duplicate filters by the alkaline dot blot method disclosed in *Proc. Nat'l Acad. Sci. USA* 85:1629 (1988). The duplicate filters are prehybridized and hybridized at 44° C., one with the Leber's probe and the other with the wild-type. To eliminate non-specific hybridization, the filter with the Leber's probe is washed at 47°-49° C. and the filter with the wild-type is washed at 49°-51° C. After autoradiography, the samples from the Leber's patients containing the mutant base at nt11778 are strongly reactive with the Leber's probe and non-reactive or only very faintly reactive with the wild-type probe. Conversely, the non-mutant mtDNA samples react strongly only with the wild-type probe and not with the mutant probe. The two duplicate filters from each test individual show reciprocal hybridization.

d. Differential PCR

Two differential PCR primers were synthesized (2→ and 3← in Table 1) with the 11778 nucleotide at the 3' end (underlined in Table 1). The 2→ primer has the nucleotide found in the Leber's mutation; the other primer, 3←, has the nucleotide found in normal mtDNA. Two other primers, 1→ and 4←, are used to generate a control "Master" fragment to confirm the presence of the appropriate region of mtDNA. Each of these primers (1→ and 4←) also pairs with one of the differential primers that will extend only Leber's or normal DNA.

TABLE 1

| PRIMERS | $T_H$ | (5'→ 3') | 5'FOR | 3' | 5'REV |
|---|---|---|---|---|---|
| 1→ | 60 | (CCCACCTTGGCTATCATCACC) | 11141 | 11161 | |
| 2→ | 59 | (CTACGAACGCACTCACAGTCA) | 11758 | 11778 | |
| 3← | 59 | (CCTTGAGAGAGGATTATGATGC) | | 11778 | 11799 |
| 4← | 59 | (GAAGCTTAGGGAGAGCTGGG) | | 12557 | 12576 |

The three primer combinations are used against the test individual's DNA template in separate PCR reactions and subjected to 35 cycles of denaturing (94° C. for 1 minute), a brief annealing at the predicted specific hybridization temperature (59°-60° C., 30 seconds), followed by a period of DNA extension (72° C., 30 seconds). The annealing step must be brief enough and at a high enough temperature to guarantee that only the exact DNA match will anneal and polymerize along the test DNA template.

PCR results are viewed on an ethidium bromide-stained 1.3% agarose gel. A sample from a person with only normal DNA would show two PCR products: the control 1435-bp fragment and the 658-bp wildtype-specific fragment (FIG. 2). A sample from a person with the mutant mtDNA would show two PCR products: the control 1435-bp fragment and the 818-bp Leber's specific fragment. An individual possessing a mixture of mutant and wildtype mtDNAs would show all three fragments: the control 1435-bp fragment, the 658-bp wildtype-specific fragment, and the 818-bp Leber's specific fragment.

TABLE 2

| PRIMERS | EXPECTED PCR PRODUCTS | SIZE | COORDINATES |
|---|---|---|---|
| (1-4) | Master Fragment | 1435 | 11141-12576 |
| (1-3) | Wildtype Fragment | 658 | 11141-11799 |
| (2-4) | LHON Fragment | 818 | 11758-12576 |

With certain specific primer designs for this and other disease loci, all three primer combinations may be combined in one PCR reaction. However, in some cases, this combination can lead to PCR artifacts, that is, extra PCR products that are not the specific targeted sequence.

What is claimed is:

1. A method of detecting neuromuscular disease that is associated with a point mutation at mitochondrial DNA nucleotide position 11778 in a patient comprising the steps of:
   a) obtaining mitochondrial DNA from a biological sample from said patient; and
   b) ascertaining the presence of said point mutation at said nucleotide position 11778 of said mitochondrial DNA to detect neuromuscular disease that is associated with said point mutation, wherein the presence of said point mutation is ascertained by a method selected from the group consisting of a restriction endonuclease method a hybridization method and an amplification method.

2. The method of claim 1, wherein said neuromuscular disease is Leber's hereditary optic neuropathy.

3. The method of claim 1, wherein said point mutation causes said neuromuscular disease.

4. The method of claim 1, wherein said point mutation is associated with said neuromuscular disease as a risk factor.

5. The method of claim 1, wherein said biological sample contains any cell from said patient.

6. The method of claim 5, wherein said cell is selected from the group consisting of a blood cell, blood platelet, white blood cell, transformed lymphoblast, hair follicle cell, epidermal cell, urinary tract cell, cerebrospinal fluid cell, chorionic villae cell, muscle cell, brain cell, liver cell, kidney cell, heart cell, and amniocentesis fluid cell.

7. The method of claim 1, wherein said point mutation changes a guanine to adenine at said 11778 position.

8. The method of claim 1, wherein said point mutation converts the 340th amino acid of NADH dehydrogenase subunit 4 from an arginine to a histidine.

9. The method of claim 1, wherein said point mutation eliminates an endonuclease restriction site.

10. The method of claim 9, wherein said endonuclease is SfaN1.

11. The method of claim 1, wherein said point mutation creates an endonuclease restriction site.

12. The method of claim 11, wherein said endonuclease in Mae 3.

13. The method of claim 1, wherein said restriction endonuclease method comprises the steps of:
    (a) digesting said mitochondrial DNA with a restriction endonuclease, selected from the group consisting of an endonuclease whose recognition site comprises a normal mitochondrial DNA sequence encompassing nucleotide position 11778 and an endonuclease whose recognition site comprises a mutant mitochondrial DNA sequence encompassing nucleotide position 11778;
    (b) separating the resulting mitochondrial DNA fragments; and (c) determining the length of said fragments to detect the presence of said point mutation at said 11778 position.

14. The method of claim 13, wherein said mitochondrial DNA from said sample is selected from the group consisting of crude complete DNA, purified complete DNA, amplified complete DNA, crude partial DNA, purified partial DNA, and amplified partial DNA.

15. The method of claim 13, wherein said endonuclease is SfaN1.

16. The method of claim 13, wherein said endonuclease is Mae 3.

17. The method of claim 13, wherein said separating step is selected from the group consisting of agarose electrophoresis followed by Southern blotting, end-labeling said fragments followed by polyacrylamide gel electrophoresis, and development of the digested products on agarose gels following amplification and digestion of said mitochondrial DNA.

18. The method of claim 1, wherein said hybridization method comprises the steps of:
(a) obtaining a differential hybridization oligonucleotide probe that is complementary to the nucleotide sequence of one strand of test mitochondrial DNA in the region surrounding said nucleotide position 11778, wherein said test mitochondrial DNA is selected from the group consisting of normal DNA that is not mutated at the 11778 position and mutant DNA that is mutated at the 11778 position;
(b) hybridizing said probe with said mitochondrial DNA from said patient; and
(c) determining the extent of said hybridization to detect the presence of said point mutation at said 11778 position.

19. The method of claim 18, wherein said probe ranges from 17 to 23 nucleotide units in length.

20. The method of claim 18, wherein said probe that is complementary to said normal DNA has the nucleotide sequence GATTATGATGCGACTGTGA such that nucleotide C at nt11778 is the differential nucleotide.

21. The method of claim 18, wherein said probe that is complementary to said mutant DNA has the nucleotide sequence TCACAGTCACATCATAATC such that nucleotide A at nt11778 is the differential nucleotide.

22. The method of claim 18, wherein said mitochondrial DNA from said sample is selected from the group consisting of crude complete DNA, purified complete DNA, amplified complete DNA, crude partial DNA, purified partial DNA, and amplified partial DNA.

23. The method of claim 1, wherein said amplification method comprises the steps of:
a) obtaining a first oligonucleotide primer that is capable of binding to normal mitochondrial DNA that is not mutated at the 11778 position such that the 3' end of said first primer is located at said 11778 nucleotide position of said normal mitochondrial DNA;
(b) obtaining a second oligonucleotide primer that is capable of binding to mutant mitochondrial DNA that is mutated at the 11778 position such that the 3' end of said second primer is located at said 11778 nucleotide position of said mutant mitochondrial DNA;
(c) obtaining a third oligonucleotide primer that is capable of pairing with said first primer to amplify said normal mitochondrial DNA in a polymerase chain reaction;
(d) obtaining a fourth oligonucleotide primer that is capable of pairing with said second primer to amplify said mutant mitochondrial DNA in a polymerase chain reaction;
(e) combinating said first, second, third, and fourth primers with said mitochondrial DNA from said patient in a polymerase chain reaction; and
(f) determining the extent of amplification of said patient's DNA to detect the presence of said point mutation at said 11778 position.

24. The method of claim 23, wherein said first primer, said second primer, said third primer, and said fourth primer range from 17 to 19 nucleotide units in length.

25. The method of claim 23, wherein said mitochondrial DNA from said sample is selected from the group consisting of crude complete DNA, purified complete DNA, amplified complete DNA, crude partial DNA, purified partial DNA, and amplified partial DNA.

26. A method of detecting neuromuscular disease that is associated with a point mutation at mitochondrial DNA nucleotide position 11778 in a patient comprising the step of ascertaining the presence of said point mutation at said nucleotide position 11778 of mitochondrial DNA obtained from a biological sample from said patient, wherein said ascertaining step comprises:
(a) obtaining mitochondrial DNA from said sample;
(b) digesting said mitochondrial DNA with a restriction endonuclease, selected from the group consisting of an endonuclease whose recognition site comprises a normal mitochondrial DNA sequence encompassing nucleotide position 11778 and an endonuclease whose recognition size comprises a mutant mitochondrial DNA sequence encompassing nucleotide position 11778;
(c) separating the resulting mitochondrial DNA fragments; and
(d) determining the length of said fragments to detect the presence of said point mutation at said 11778 position.

27. A method of detecting neuromuscular disease that is associated with a point mutation at mitochondrial DNA nucleotide position 11778 in a patient comprising the step of ascertaining the presence of said point mutation at said nucleotide position 11778 of mitochondrial DNA obtained from a biological sample from said patient, wherein said ascertaining step comprises:
(a) obtaining mitochondrial DNA from said sample;
(b) obtaining a hybridization oligonucleotide probe that is complementary to the nucleotide sequence of one strand of test mitochondrial DNA in the region surrounding said nucleotide position 11778, wherein said test mitochondrial DNA is selected from the group consisting of normal DNA that is not mutated at the 11778 position and mutant DNA that is mutated at the 11778 position;
(c) hybridizing said probe with said mitochondrial DNA from said patient; and
(d) determining the extent of said hybridization to detect the presence of said point mutation at said 11778 position.

28. A method of detecting neuromuscular disease that is associated with a point mutation at mitochondrial DNA nucleotide position 11778 in a patient comprising the step of ascertaining the presence of said point mutation at said nucleotide position 11778 of mitochondrial DNA obtained from a biological sample from said patient, wherein said ascertaining step comprises:
(a) obtaining mitochondrial DNA from said sample;
(b) obtaining a first oligonucleotide primer that is capable of binding to normal mitochondrial DNA that is not mutated a the 11778 position such that the 3' end of said first primer is located at said 11778 nucleotide position of said normal mitochondrial DNA;
(c) obtaining a second oligonucleotide primer that is capable of binding to mutant mitochondrial DNA that is mutated at the 11778 position such that the 3' end of said second primer is located at said 11778 nucleotide position of said mutant mitochondrial DNA;
(d) obtaining a third oligonucleotide primer that is capable of pairing with said first primer to amplify said normal mitochondrial DNA in a polymerase chain reaction;
(e) obtaining a fourth oligonucleotide primer that is capable of pairing with said second primer to amplify said mutant mitochondrial DNA in a polymerase chain reaction;
(f) combining said first, second, third and fourth primers with said mitochondrial DNA from said patient in a polymerase chain reaction; and
(g) determining the extent of amplification of said patient's DNA to detect the presence of said point mutation at said 11778 position.

29. An oligonucleotide probe that selectively hybridizes to normal or mutant mitochondrial DNA to detect the presence of a point mutation at mitochondrial DNA nucleotide position 11778 in a biological sample from a patient, consisting essentially of about 10 to about 42 consecutive nucleotides, including the nucleotide corresponding to said 11778 position, selected from the group of nucleotide sequences consisting of:

CTACGAACGC ACTCACAGTC G CATCATAAT CCTCTCTCAA GG;

GATGCTTGCG TGAGTGTCAG C GTAGTATTA GGAGAGAGTT CC;

CTACGAACGC ACTCACAGTC A CATCATAAT CCTCTCTCAA GG;

and

GATGCTTGCG TGAGTGTCAG T GTAGTATTA GGAGAGAGTT CC.

30. The probe of claim 29, wherein said probe contains less than about 35 nucleotides.

31. The probe of claim 29, wherein said probe is complementary to the nucleotide sequence of one strand of normal human mitochondrial DNA in the region surrounding said nucleotide position 11778 and including said position.

32. The probe of claim 29, wherein said probe, is complementary to and flanks said nucleotide position 11778 of one strand of normal human mitochondrial DNA and can direct replication of said position.

33. The probe of claim 29, wherein said probe is complementary to normal human mitochondrial DNA and the 3' end of said probe is located at said 11778 nucleotide position of normal human mitochondrial DNA.

34. The probe of claim 29, wherein said probe is complementary to the nucleotide sequence of one strand of mutant human mitochondrial DNA in the region surrounding said nucleotide position 11778 and including said position.

35. The probe of claim 29, wherein said probe is complementary to and flanks said nucleotide position 11778 of one strand of mutant human mitochondrial DNA and can direct replication of said position.

36. The probe of claim 29, wherein said probe is complementary to human mitochondrial DNA and the 3' end of said probe is located at said 11778 nucleotide position of mutant human mitochondrial DNA.

* * * * *